United States Patent
Benvenuti et al.

(10) Patent No.: US 7,132,556 B2
(45) Date of Patent: Nov. 7, 2006

(54) ALKALINE EARTH METAL COMPLEXES AND THEIR USE

(75) Inventors: Federica Martina Benvenuti, Brussels (BE); Dominique Jan, Beaufays (BE)

(73) Assignee: Solvay Barium Strontium GmbH, Hannover (DE)

( * ) Notice: Subject to any disclaimer, the term of this patent is extended or adjusted under 35 U.S.C. 154(b) by 118 days.

(21) Appl. No.: 11/022,674

(22) Filed: Dec. 28, 2004

(65) Prior Publication Data

US 2005/0170092 A1 Aug. 4, 2005

Related U.S. Application Data

(63) Continuation of application No. PCT/EP03/006501, filed on Jun. 20, 2003.

(30) Foreign Application Priority Data

Jun. 28, 2002 (DE) .............................. 102 29 040

(51) Int. Cl.
- C07F 3/00 (2006.01)
- C23C 16/00 (2006.01)
- C07C 323/23 (2006.01)

(52) U.S. Cl. .................. 556/32; 564/502; 564/511; 427/248.1; 427/255.19

(58) Field of Classification Search .................. 556/32; 564/502, 511; 427/248.1, 255.19
See application file for complete search history.

(56) References Cited

U.S. PATENT DOCUMENTS

- 3,594,216 A * 7/1971 Charles et al. .............. 427/252
- 5,008,415 A 4/1991 Norman ...................... 556/32
- 5,451,434 A 9/1995 Doellein
- 6,620,971 B1 * 9/2003 Chang et al. ................ 564/502

FOREIGN PATENT DOCUMENTS

- DE 41 20 344 A1 1/1992
- EP 369297 5/1990
- JP 09-136857 A 5/1997
- WO WO 2004002946 A1 * 1/2004

OTHER PUBLICATIONS

Daniel B. Studebaker, et al., "Encapsulating Bis(β-Ketoiminato) Polyethers. Volatile, Fluoride-Free Barium Precursors for Metal-Organic Chemical Vapor Deposition", Inorganic Chemistry, 2000, pp. 3148-3157, 39, American Chemical Society.

William S. Rees, Jr., et al., "Alkoxyalkyl-Substituted β-Diketonate Complexes of Barium and Copper: Evidence for Inter- and Intramolecular Stabilization", Angew. Chem. Int. Ed. Engl., 1992, pp. 735-736, 31, No. 6, Weinheim.

F. Albert Cotton, et al., The First Complex with a $_o^2$ $n^4$ Triple Bond between Vanadium Atoms in a Ligand Framework of Fourfold Symmetry-[$V_2${(p-$CH_3C_6H_4$)NC(H)N(p-$C_6H_4CH_3$)}$_4$].

Schulz, et al., "Barium β-Ketoiminate Complexes Containing Appended Ether "Lariats". Synthesis, Characterization, and Implementation as Fluorine-Free Barium MOCVD Precursors", Chem. Mater, 1993, 5,1605-1617.

Neumayer et al, Approaches to Alkaline Earth Metal-Organic Chemical Vapor Deposition Precursors, Synthesis and Characterization of Barium Fluoro-β-ketoiminate Complexes Having Appended Polyether "Lariats", Inorg. Chem. 1998, 37, 5625-5633.

* cited by examiner

*Primary Examiner*—Porfirio Nazario-Gonzalez
(74) *Attorney, Agent, or Firm*—Crowell & Moring LLP

(57) ABSTRACT

Chelate complexes of calcium, strontium and barium formed with ligands that are beta-ketiminate compounds having a scorpion tail; intermediate compounds useful in producing the aforementioned complexes; a method for producing such complexes, and the use of such complexes for depositing layers containing calcium, barium or strontium.

19 Claims, No Drawings

ALKALINE EARTH METAL COMPLEXES AND THEIR USE

CROSS REFERENCE TO RELATED APPLICATIONS

This application is a continuation of international patent application No. PCT/EP03/006501, filed Jun. 20, 2003, designating the United States of America, and published in German as WO 2004/002946 on Jan. 8, 2004, the entire disclosure of which is incorporated herein by reference. Priority is claimed based on Federal Republic of Germany patent application No. DE 102 29 040.7, filed Jun. 28, 2002.

BACKGROUND OF THE INVENTION

The present invention relates to new, vaporizable chelate complexes of calcium, barium and strontium, to a method for their synthesis, to their use for depositing layers containing calcium, barium or strontium and to intermediates for synthesizing the compounds.

Metal-organic chemical vapor deposition (MOCVD) is a method, which can be used very well for depositing layers containing metal or metal compounds. It is the method of choice for depositing ceramic thin-layers for a plurality of electronic components. Examples are ferroelectric layers based on barium titanate or barium strontium titanate. Such layers are used, for example, for DRAM components.

For this application, as well as for other applications, it is desirable that the organometallic alkaline earth compounds have a high volatility, which facilitates sublimation and the transport to the place of deposition, that they can be decomposed thermally at relatively low temperatures, such as those of the order of 450° C., and that, for certain application areas, they are deposited in the form of the oxides and not, for example, in the form of other decomposition products such as carbonates.

Alkaline earth metal beta-diketonates and certain derivatives have already been used for the MOCVD method. Classical examples are complexes of alkaline earth metals with 1,1,6,6-tetramethylheptanedionate. However, such complexes may be present as oligomers, the volatility and stability of which are unsatisfactory. In order to improve these properties, the tetramethylheptane dionate complex compounds were used in the form of Lewis base adducts, for example, as adduct with polyethers or polyamines. Such complexes, however, still have stability problems. Barium compounds and strontium compounds with ligands, which have three coordination sites, have also been proposed.

SUMMARY OF THE INVENTION

It is an object of the present invention to provide new alkaline earth metal compounds.

Another object of the invention is to provide alkaline earth metal compounds which are very suitable for metal-organic chemical vapor-phase deposition.

A further object is to provide alkaline earth metal compounds which are particularly suitable for producing ceramic thin-films.

These and other objects are achieved in accordance with the present invention by providing a compound corresponding to formula (I)

$$M(R)_2 \quad (I)$$

wherein
M represents calcium, strontium or barium, and
R represents a beta-ketiminate compound,
  in which the nitrogen atom of the imine function is substituted by $(CH_2)_m NR^1_2$, wherein
  m is 2 to 4, and
  $R^1$ is a C1–C3 alkyl group,
  and in which the carbon chain of the beta-ketiminate group is substituted by $R^2O(CH_2)_n$, wherein
  $R^2$ is C1–C3 alkyl, and
  n is 2 to 4.

In accordance with a further aspect of the invention, the objects are also achieve by providing a method of synthesizing a compound corresponding to formula (I)

$$M(R)_2 \quad (I)$$

wherein
M represents calcium, strontium or barium, and
R represents a beta-ketiminate compound,
  in which the nitrogen atom of the imine function is substituted by $(CH_2)_m NR^1_2$, wherein
  m is 2 to 4, and
  $R^1$ is a C1–C3 alkyl group,
  and in which the carbon chain of the beta-ketiminate group is substituted by $R^2O(CH_2)_n$, wherein
  $R^2$ is C1–C3 alkyl, and
  n is 2 to 4;

said method comprising:
  reacting metallic calcium, barium or strontium or a hydride thereof with a beta-ketimine compound of formula RH, wherein R has the meaning given above, or
  reacting a salt of calcium, strontium or barium with a salt which contains the group R as an anion.

In accordance with yet another aspect of the invention, the objects are achieved by providing a method for depositing a layer containing an alkaline earth metal on a substrate, said method comprising decomposing a compound corresponding to formula (I)

$$M(R)_2 \quad (I)$$

wherein
M represents calcium, strontium or barium, and
R represents a beta-ketiminate compound,
  in which the nitrogen atom of the imine function is substituted by $(CH_2)_m NR^1_2$, wherein
  m is 2 to 4, and
  $R^1$ is a C1–C3 alkyl group,
  and in which the carbon chain of the beta-ketiminate group is substituted by $R^2O(CH_2)_n$, wherein
  $R^2$ is C1–C3 alkyl, and
  n is 2 to 4;

in the presence of the substrate.

In a still further aspect of the invention, the objects are achieved by providing a compound corresponding to the formula $$RH$$

wherein
R represents a beta-ketiminate group
  in which the nitrogen atom of the imine function is substituted by $(CH_2)_m NR^1_2$, wherein
  m is 2 to 4, and
  $R^1$ represents a C1–C3 alkyl group;

and in which the carbon chain of the beta-ketiminate group is substituted by $R^2O(CH_2)_n$, wherein
$R^2$ is C1–C3 alkyl and
n is 2 to 4.

The compounds of the invention correspond to formula (I), $M(R)_2$, in which M represents calcium, strontium and barium and R represents a beta-ketiminate compound (that is, the ligand has a keto group and an in imino group), in which the nitrogen atom of the imine function is substituted by a group having the formula $(CH_2)_mNR^1_2$, in which m is 2 to 4 and $R^1$ is a C1–C3 alkyl group, and in which the carbon chain is substituted by $R^2O(CH_2)_n$, in which $R^2$ is C1–C3 alkyl and n is 2 to 4.

Preferably, M represents strontium and barium. The invention is explained further by means of this preferred embodiment.

In the compounds of the invention corresponding to formula I, the anions have four coordination sites for interacting with the metal cation, namely the keto group, the imino group, the nitrogen atom of the aminoalkyl group which is linked to the imine function, and the oxygen atom of the alkoxyalkyl group which is linked to the carbon backbone and, moreover, preferably via the carbon atom of the ketimine group.

Particularly preferred are compounds of formula (Ia)

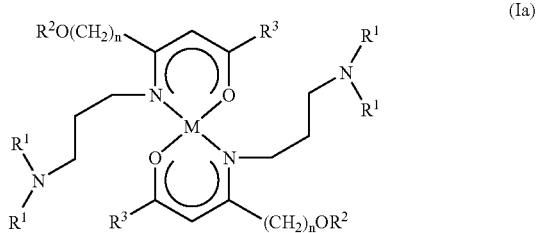

In the compounds of formula (Ia), m represents calcium and preferably barium and strontium, $R^1$ and $R^2$ have the meanings given above, and $R^3$ represents C1–C4 alkyl. The symmetrical reproduction of the drawing of the molecule is not intended to imply that there actually is a symmetrical arrangement of the atoms in the three-dimensional molecule. The lines drawn between the nitrogen and oxygen atoms and the metal cation indicate that the interaction between them is assumed to be particularly strong.

The $R^1$ groups at the nitrogen atoms may be the same or different. Preferably, however, they are the same end represent, in particular, methyl or ethyl. Preferably, $R^3$ represents t-butyl and n is 3.

In order to synthesize the compounds of the invention, the metallic alkaline earth metal or a hydride thereof, which advantageously is finely divided, can be reacted with the ketimine compound RH, which corresponds to the above-described ligand R. The acidic proton is reduced to hydrogen; the alkaline earth metal is oxidized to the alkaline earth metal cation; the hydride is oxidized to hydrogen, and the desired complex compound according to the invention is formed. Alternatively, an alkaline earth metal salt can also be reacted with a salt, which contains the ligand as an anion, such as the lithium salt (obtainable by reacting BuLi with the ligand).

In order to synthesize the preferred compounds which correspond to formula (Ia), the corresponding N',N'-dialkylaminoalkylimino-8-alkoxy-5-alkanone compound is reacted quite similarly with the finely divided alkaline earth metal or the hydride. The synthesis of barium(II) bis(2,2-dimethyl-5-N-(N'N'-dimethylaminoopropylimino-8-methoxy-5-octanoate and strontium(II) bis(2,2-dimethyl-5-N-(N',N'-dimethylaminopropylimino)-8-methoxy-octanoate in this way is particularly preferred.

The ketimine compounds of formula RH, which can be used for the synthesis of the complex compounds and in which R has the meaning given above, and which are, in particular, N'N'-(dialkylaminoalkylimino)-8-alkoxy-5-alkanone compounds of formula (II), are also new and, as important intermediates, also an object of the invention.

In formula (II) of $R^2O(CH_2)_nC(NCH_2CH_2CH_2NR^1_2)$ $CH_2C(O)R^3$, $R^1$, $R^2$, $R^3$ and n have the meanings given above.

The ketimine compounds can be synthesized as described below. To begin with, the beta-diketo compound, corresponding to the ketimine compound, is synthesized. The synthesis can be carried out by the Claisen condensation of a ketone width an omega-alkoxycarboxylate ester. For this reaction, the ketone and the omega-alkoxycarboxylate ester are selected, so that the alkyl group of the ketone, the alkyl group of the omega-alkoxy group and the alkyl chain between the omega-alkoxy group and the ester function correspond to the desired substituents in the ketimine compound, which is to be synthesized. The Claisen condensation is carried out by heating in the presence of sodium hydride in a solvent, such as dimethoxyethane. The reaction mixture can be worked up, for example, with aqueous hydrochloric acid.

The resulting beta-diketo compound is reacted at an elevated temperature with a diamine of the desired chain length. A nitrogen atom of this diamine must be substituted by two hydrogen atoms and reacts with a keto group of the beta-diketo compound, water being split off and the desired ketimine compound being formed.

The synthesis of the ketimine compounds is described in greater detail with reference to the illustrative synthesis of 2,2-dimethyl-5-N-(N',N'-dimethylaminopropylamino)-8-methoxy-5-octanone, which is a particularly preferred ligand for complexing the alkaline earth metals. The first step comprises the synthesis of 2,2-dimethyl-8-methoxyoctane-3,5-dione. It can be carried out as described by W. S. Rees Jr., C. R. Caballero and W. Hesse in Angew. Chem. 104 (1992), No. 6, pages 786 to 788.

$(CH_3)_3CC(O)CH_3$ (pinacolone) and $CH_3O(O)C(CH_2)_3$ $OCH_3$ are subjected to a Claisen condensation using sodium hydride. The 2,2-dimethyl-8-methoxyoctane-3,5-dione obtained is then reacted with N,N-dimethylaminopropylamine to form the desired 2,2-dimethyl-5-N-(N',N'-dimethylaminopropylimino)-8-methoxy-5-octanone.

Other ketimine compounds can be produced similarly. The ketimine compounds can be used not only for the synthesis of barium, strontium or calcium complex compounds, but also for the synthesis of compounds or complexes with other metals.

The alkaline earth metal complexes according to the invention can be used for those applications, in which alkaline earth metal organic compounds are used with the objective of depositing an alkaline earth metal. The concept of "alkaline earth metal deposition" is not limited to metallic alkaline earth metals, but is intended to include also and especially cations of alkaline earth metals.

A preferred area of use for the alkaline earth metal complexes of the invention is the deposition of layers which contain the alkaline earth metal in the form of an oxide. The use of the alkaline earth metal complexes according to the invention is especially preferred in the MOCVD processes for the preparation of thin layers, which contain the alkaline earth metal, preferably barium and/or strontium, in oxide form. Such layers are used, for example, in high-temperature superconductor technology. Examples include barium titanate and barium strontium titanate layers. Layers of this type are required, for example, in DRAM technology. Such DRAMs have sockets of polysilicon and, insulated by a nitride layer, have a platinum coating. The platinum layer is covered by a barium strontium titanate layer. This can be accomplished with the alkaline earth metal complexes of the invention using the MOCVD process. MOCVD processes are usually carried out in vacuum equipment, in which the alkaline earth metal complex compound or a mixture of such compounds is vaporized at a low pressure. The complex compound is then decomposed. In the case of the inventive alkaline earth metal complex, ceramic layers, which contain the alkaline earth metal in oxide form, are deposited on the substrate, for example, the DRAM. The thermal decomposition can also be induced by radiation or photolysis. A further decomposition method is the plasma-induced decomposition (See also, U.S. Pat. No. 5,451,434).

The decomposition preferably is carried out in an inert gas, such as nitrogen or argon. Optionally, a reactive gas, such as oxygen, can also be used. This may help to obtain good oxide layers. Of course, an oxidative post-treatment may also be provided.

If, in addition, other metals are to be deposited, other conventional commercial metal compounds, such as titanium compounds, can be used prior to, simultaneously with, or after the decomposition. Examples of suitable complexes with other metals include the amine pyrrolyl titanium compounds listed in German patent no. DE 41 20 344.

The alkaline earth metal complexes of the invention are especially advantageous when used in the MOCVD process, because they are already volatile at low temperatures, are thermally stable, have a stable vapor pressure and can be decomposed cleanly to form ceramic oxide layers. The compounds can be used very well even in the presence of moisture.

The following working examples are intended to illustrate the invention in further detail, without limiting its scope.

EXAMPLES

Example 1

Synthesis of 2,2-dimethyl-5-N-(N',N'-dimethylaminopropylimino)-8-methoxy-5-octanone Example 1.1

Synthesis of 2,2-dimethyl-8-methoxyoctane-3,5-dione

Reaction Equation:

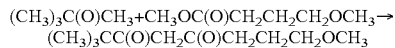

(CH$_3$)$_3$C(O)CH$_3$+CH$_3$OC(O)CH$_2$CH$_2$CH$_2$OCH$_3$→
(CH$_3$)$_3$CC(O)CH$_2$C(O)CH$_2$CH$_2$CH$_2$OCH$_3$

CH$_3$O(CH$_2$)$_3$C(O)CH$_3$ (40 ml, 38.76 g, 0.2933 moles), dissolved in approximately 160 ml of freshly distilled dimethoxy ether and 12.49 g (0.541 moles) of sodium hydride were added to a round-bottom flask equipped with a reflux condenser, a dropping funnel with pressure equalization and a magnetic stirrer. The solution was stirred and anhydrous pinacolone (44 ml, 35.2 44 g, 0.352 moles) was added dropwise. At the end of the addition, the mixture was refluxed. After 18 hours, the reaction mixture was cooled to room temperature and approximately 56 ml of concentrated hydrochloric acid were added carefully. The 2-phase mixture was added to a phase separator. The aqueous phase was extracted twice with 100 ml portions of diethyl ether. The combined organic extracts were washed twice with 100 ml portions of dilute sodium hydroxide solution (1% by weight in water) and finally with water. The organic phase was dried over anhydrous magnesium sulfate. After the filtration, the solvent was removed under reduced pressure. The pure product was obtained by distilling the residue (boiling point approximately 45° to 47° C. at 0.01 mm Hg).

Yield: 29.3 g (49.8% of the theoretical yield)

Analysis:
$^1$H-NMR (CDCL$_3$-300 k)•(ppm)=5.58 (s, 1H, CH diketone); 3.36 (t, 2H, C$\underline{H}_2$—O); 3.30 (s, 3H, —OC$\underline{H}_3$); 2.36 (t, 2H, —C$\underline{H}_2$ ketone side); 1.84 (p, 2H, —C$\underline{H}_2$ central); 1.11 (s, 9H, —C$\underline{H}_3$, t-butyl) in ppm against TMS Example 1.2

Synthesis of 2,2-dimethyl-5-N-(N',N'-dimethylaminopropylimino)-8-methoxy-5-octanone Reaction Equation:

(CH$_3$)$_3$CC(O)CH$_2$C(O)CH$_2$CH$_2$CH$_2$OCH$_3$+(CH$_3$)$_2$NCH$_2$CH$_2$CH$_2$NH$_2$→(CH$_3$)$_3$CC(O)CH$_2$C[NCH$_2$CH$_2$CH$_2$N(CH$_3$)$_3$)$_3$]CH$_2$CH$_2$CH$_2$OCH$_3$

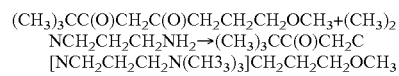

Method:
The 2,2-dimethyl-8-methoxy-3,5-octanedione (7.7399 g, 38.6 mmoles), synthesized in Example 1.1), and 4.9 ml (3.9 79 g, 38.9 mmoles) of freshly distilled N,N-dimethylaminopropylamine were added to a 25 ml round-bottom flask under an atmosphere of dry nitrogen. The flask was equipped with a reflux condenser and a magnetic stirrer. The solution was refluxed (130° C.) for 18 hours with vigorous stirring. Subsequently, the mixture was cooled to room temperature, and an equivalent volume of demineralized water was added. The aqueous phase was then extracted twice with 25 ml portions of diethyl ether, and the combined organic extracts were dried over anhydrous magnesium sulfate. After the filtration, the solvent was removed under vacuum, and the residue was distilled in a dynamic vacuum.

Yield: 9.22 g (32.4 mmoles) of a colorless liquid (84% of the theoretical yield).

Analysis:
$^1$H-NMR (CDCl$_3$-300K)·(ppm)=11.0 (s, 1 h, wide —OH); 5.15 (s, 1H, —C$\underline{H}$—·-ketoimine); 3.42 (t, 2H, C$\underline{H}_2$—O); 3.36 (s, 3H, —OC$\underline{H}_3$); 3.28 (q, 2H, —C$\underline{H}_2$—); 1.12 (s, 9H, —C$\underline{H}_3$ t-butyl) in ppm against TMS as standard.

Example 2

Synthesis of Barium and Strontium Complexes

Example 2.1

Synthesis of Barium(II) bis-(2,2-dimethyl-5-N-(N',N'-dimethylaminopropylamino)-8-methoxy-5-octanoate)

Method:
Finely divided metallic barium (0.807 g, 5.88 mmoles) and 3.714 g (13.1 mmoles) of the octanone, synthesized in Example 1.2, were added under an atmosphere of dry nitrogen to a 25 mL round-bottom flask, which was equipped with a mechanical stirrer. The suspension was stirred at room temperature, until the solid metallic barium had finished reacting. A highly viscous brown oil was obtained after a reaction time of about one week.

Yield: 4.1 g (5.8 mmoles) of a dark red, viscous oil (99% of the theoretical yield).

Analytical Data:

Elemental analysis: C=52.7 (theoretical: 54.6); H=8.7 (theoretical: 8.9); N=7.6 (theoretical: 8.0); the data is given in percent by weight.

Under nitrogen, evaporation commences at about 200° C. The evaporation behavior is no worse in the presence of 5 ppm of water.

Example 2.2

Synthesis of Strontium(II) bis-(2,2-dimethyl-5-N-(N',N'-dimethylaminopropylimino)-8-methoxy-5-octanoate)

Method:

Finely divided metallic strontium (0.708 g, 8.08 mmoles) and 4.92 g (17.3 mmoles) of the octanone, synthesized in Example 1.2, were added under an atmosphere of dry nitrogen to a 25 ml round-bottom flask, which was equipped with a mechanical stirrer. The suspension was stirred at room temperature, until the solid metallic strontium had finished reacting. A highly viscous oil was obtained after a reaction time of about one week.

Yield: 5.28 g (8.1 mmoles) of a dark red, viscous oil (99% of the theoretical yield).

Under nitrogen, the evaporation commences noticeably at a temperature of at least 210° C. A steady evaporation rate was observed at temperatures of 125° and 150° C. for a period of 250 minutes, even in the presence of 5 ppm of water. The compound accordingly is very stable thermally.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula (I)

$$M(R)_2 \quad (I)$$

wherein

M represents calcium, strontium or barium, and

R represents a beta-ketiminate compound, in which the nitrogen atom of the imine function is substituted by $(CH_2)_m NR^1{}_2$, wherein m is 2 to 4, and $R^1$ is a C1–C3 alkyl group, and in which the carbon chain of the beta-ketiminate group is substituted by $R^2O(CH_2)_n$, wherein $R^2$ is C1–C3 alkyl, and n is 2 to 4.

2. A compound according to claim 1, corresponding to formula (Ia)

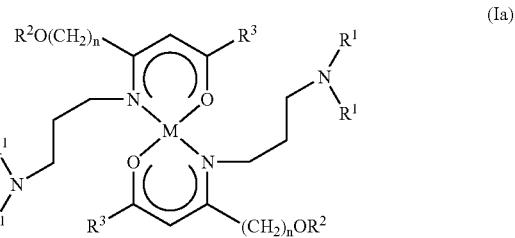

wherein M, n, $R^1$ and $R^2$ have the meanings given above, and $R^3$ represents C1–C4 alkyl.

3. A compound according to claim 1, wherein $R^1$ is methyl or ethyl.

4. A compound according to claim 1, wherein $R^2$ is methyl or ethyl.

5. A compound according to claim 2, wherein $R^3$ is t-butyl.

6. A compound according to claim 1, wherein n is 3.

7. A method of synthesizing a compound corresponding to formula (I)

$$M(R)_2 \quad (I)$$

wherein

M represents calcium, strontium or barium, and

R represents a beta-ketiminate compound, in which the nitrogen atom of the imine function is substituted by $(CH_2)_m NR^1{}_2$, wherein m is 2 to 4, and $R^1$ is a C1–C3 alkyl group, and in which the carbon chain of the beta-ketiminate group is substituted by $R^2O(CH_2)_n$, wherein $R^2$ is C1–C3 alkyl, and n is 2 to 4;

said method comprising:

reacting metallic calcium, barium or strontium or a hydride thereof with a beta-ketimine compound of formula RH, wherein R has the meaning given above, or reacting a salt of calcium, strontium or barium with a salt which contains the group R as an anion.

8. A method according to claim 7, for synthesizing a compound corresponding to formula (Ia)

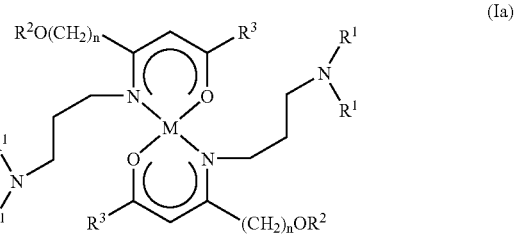

wherein metallic calcium, barium or strontium is reacted with a beta-ketimine compound corresponding to formula (II)

$$R^2O(CH_2)_n C(NCH_2CH_2CH_2NR^1{}_2)CH_2C(O)R^3 \quad (II)$$

wherein $R^1$, $R^2$ and n have the meanings given above, and $R^3$ represents C1–C4 alkyl.

9. A method for depositing a layer containing an alkaline earth metal on a substrate, said method comprising decomposing a compound corresponding to formula (I)

$$M(R)_2 \quad (I)$$

wherein
M represents calcium, strontium or barium, and
R represents a beta-ketiminate compound,
in which the nitrogen atom of the imine function is substituted by $(CH_2)_m NR^1{}_2$, wherein
m is 2 to 4, and
$R^1$ is a C1–C3 alkyl group,
and in which the carbon chain of the beta-ketiminate group is substituted by $R^2O(CH_2)_n$, wherein
$R^2$ is C1–C3 alkyl, and
n is 2 to 4;
in the presence of the substrate.

10. A method according to claim 9, wherein a compound corresponding to formula (Ia)

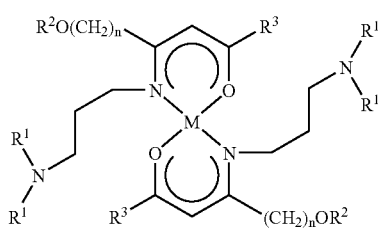

wherein
M, n, $R^1$ and $R^2$ have the meanings given above, and
$R^3$ represents C1–C4 alkyl;
is decomposed.

11. A method according to claim 9, wherein the compound of formula (I) is evaporated and then is decomposed.

12. A method according to claim 9, wherein at least one compound of at least one further metal also is decomposed.

13. A method according to claim 12, wherein said at least one compound is a titanium compound.

14. A method according to claim 13, wherein a barium strontium titanate layer is formed.

15. A method according to claim 9, wherein said substrate is a DRAM component.

16. A compound corresponding to the formula

RH wherein
R represents a beta-ketiminate group
in which the nitrogen atom of the imine function is substituted by $(CH_2)_m NR^1{}_2$, wherein
m is 2 to 4, and
$R^1$ represents a C1–C3 alkyl group;
and in which the carbon chain of the beta-ketiminate group is substituted by $R^2O(CH_2)_n$, wherein
$R^2$ is C1–C3 alkyl and
n is 2 to 4.

17. A compound according to claim 16, corresponding to formula (II)

$$R^2O(CH_2)_nC(NCH_2CH_2CH_2NR^1{}_2)CH_2C(O)R^3 \quad (II)$$

wherein
$R^1$, $R^2$ and n having the meanings given above, and
$R^3$ represents C1–C4 alkyl.

18. A method of synthesizing a metal chelate, said method comprising reacting a metal with a compound corresponding to the formula

RH wherein
R represents a beta-ketiminate group,
in which the nitrogen atom of the imine function is substituted by $(CH_2)_m NR^1{}_2$, wherein
m is 2 to 4, and
$R^1$ is a C1–C3 alkyl group,
and in which the carbon chain of the beta-ketiminate group is substituted by $R^2O(CH_2)_n$, wherein
$R^2$ is C–C3 alkyl, and
n is 2 to 4.

19. A method according to claim 18, wherein said compound corresponds to formula (II)

$$R^2O(CH_2)_nC(NCH_2CH_2CH_2NR^1{}_2)CH_2C(O)R^3 \quad (II)$$

wherein
$R^1$, $R^2$ and n having the meanings given above, and
$R^3$ represents C1–C4 alkyl.

* * * * *